US007276087B2

(12) United States Patent
Audousset

(10) Patent No.: US 7,276,087 B2
(45) Date of Patent: Oct. 2, 2007

(54) DYE COMPOSITION COMPRISING 2-CHLORO-6-METHYL-3-AMINOPHENOL AS COUPLER, PARA-AMINOPHENOL AND 3-METHYL-4-AMINOPHENOL AS OXIDATION BASES AND AT LEAST ONE ASSOCIATIVE THICKENING POLYMER

(75) Inventor: Marie-Pascale Audousset, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/834,113

(22) Filed: Apr. 29, 2004

(65) Prior Publication Data
US 2005/0000037 A1    Jan. 6, 2005

Related U.S. Application Data

(60) Provisional application No. 60/507,120, filed on Oct. 1, 2003.

(30) Foreign Application Priority Data
Apr. 29, 2003   (FR) .................................. 03 05243

(51) Int. Cl.
*A61K 7/13*    (2006.01)
(52) U.S. Cl. .................. 8/405; 8/406; 8/410; 8/411; 8/421; 8/424; 8/515; 8/552; 8/554
(58) Field of Classification Search .............. 8/405, 8/406, 410, 411, 421, 424, 515, 552, 554
See application file for complete search history.

(56) References Cited

U.S. PATENT DOCUMENTS

| | | | |
|---|---|---|---|
| 3,915,921 A | 10/1975 | Schlatzer, Jr. .............. 760/17.4 |
| RE30,199 E | 1/1980 | Rose et al. .................... 8/10.2 |
| 4,509,949 A | 4/1985 | Huang et al. ................ 586/558 |
| 4,823,985 A | 4/1989 | Grollier et al. ................. 222/1 |
| 5,061,289 A | 10/1991 | Clausen et al. ................. 8/405 |
| 5,380,340 A | 1/1995 | Neunhoeffer et al. .......... 8/409 |
| 5,534,267 A | 7/1996 | Neunhoeffer et al. ....... 421/701 |
| 5,663,366 A | 9/1997 | Neunhoeffer et al. .... 548/321.4 |
| 5,766,576 A | 6/1998 | Löwe .............................. 424/62 |
| 6,099,592 A | 8/2000 | Vidal et al. ..................... 8/409 |
| 6,156,076 A | 12/2000 | Casperson et al. ............. 8/406 |
| 6,277,156 B1 * | 8/2001 | Audousset ...................... 8/407 |
| 6,284,003 B1 | 9/2001 | Rose et al. ...................... 8/412 |
| 6,338,741 B1 | 1/2002 | Vidal et al. ..................... 8/409 |
| 6,379,396 B1 | 4/2002 | Audousset ...................... 8/407 |
| 6,436,151 B2 | 8/2002 | Cottard et al. .................. 8/406 |
| 6,503,282 B1 | 1/2003 | Braun ............................. 8/405 |
| 6,645,258 B2 | 11/2003 | Vidal et al. ..................... 8/405 |
| 6,730,789 B1 | 5/2004 | Birault et al. ................ 546/121 |
| 6,800,098 B1 | 10/2004 | Allard et al. ................... 8/405 |
| 2001/0023514 A1 * | 9/2001 | Cottard et al. .................. 8/406 |
| 2001/0023515 A1 | 9/2001 | Cottard et al. .................. 8/406 |
| 2002/0050013 A1 | 5/2002 | Vidal et al. ..................... 8/405 |
| 2003/0019051 A9 | 1/2003 | Vidal et al. ..................... 8/405 |
| 2003/0106167 A1 | 6/2003 | Rose et al. ...................... 8/405 |
| 2003/0124079 A1 | 7/2003 | Mougin et al. ........... 424/70.11 |
| 2003/0172471 A1 | 9/2003 | Chassot et al. ................. 8/405 |
| 2004/0025266 A1 | 2/2004 | Cottard et al. .................. 8/405 |
| 2004/0049860 A1 | 3/2004 | Cottard et al. .................. 8/405 |
| 2004/0098815 A1 | 5/2004 | Schmenger et al. ............ 8/405 |
| 2004/0141943 A1 | 7/2004 | Mougin et al. ........... 424/70.17 |
| 2004/0205901 A1 | 10/2004 | Cottard et al. .................. 8/405 |
| 2005/0076458 A1 | 4/2005 | Cottard et al. .................. 8/405 |

FOREIGN PATENT DOCUMENTS

| | | |
|---|---|---|
| DE | 23 59 399 | 6/1975 |
| DE | 38 43 892 | 6/1990 |
| DE | 41 33 957 A1 | 4/1993 |
| DE | 195 43 988 A1 | 5/1997 |
| DE | 201 07 481 | 8/2001 |
| DE | 30 16 008 A1 | 10/2001 |
| DE | 201 18 982 | 1/2002 |
| EP | 0 216 479 B2 | 4/1987 |
| EP | 0 173 109 | 10/1989 |
| EP | 0 770 375 | 5/1997 |
| EP | 0 875 237 A2 | 11/1998 |
| FR | 2586913 | 3/1987 |
| FR | 2733749 | 11/1996 |
| FR | 2801308 | 5/2001 |

(Continued)

OTHER PUBLICATIONS

English language Derwent Abstract of DE 201 07 481, Aug. 16, 2001.
Co-pending U.S. Appl. No. 10/834,270, filed Apr. 29, 2004, Title: Composition Comprising at Least One Coupler Chosen From 2-Chloro-6-Methyl-3-Aminophenol and Addition Salts Thereof, at Least One Oxidation Base, and at Least One Associative Polymer Comprising at Least One C8-C30 Fatty Chain.
Office Action in Co-pending U.S. Appl. No. 10/834,270, dated Mar. 29, 2005 (Examiner Elhilo).
Co-pending U.S. Appl. No. 10/834,349, filed Apr. 29, 2004, Title: Composition Comprising at Least One Coupler Chosen From 2-Chloro-6-Methyl-3-Aminophenol and Addition Salts Thereof, at Least One Oxidation Base, and at Least One Associative Polymer Comprising at Least One $C_8$-$C_{30}$ Fatty Chain.

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The present disclosure relates to a composition for oxidation dyeing keratin fibers, for instance human keratin fibers such as the hair, comprising 2-chloro-6-methyl-3-aminophenol as at least one coupler, para-aminophenol as at least one first oxidation base, 3-methyl-4-aminophenol as at least one second oxidation base, and an associative thickening polymer.

The present disclosure also relates to a multi-compartment device or kit for the oxidation dyeing of keratin fibers comprising the compositions disclosed herein, and to the dyeing process using these compositions.

35 Claims, No Drawings

FOREIGN PATENT DOCUMENTS

| | | |
|---|---|---|
| FR | 2802089 | 6/2001 |
| FR | 2 811 993 | 1/2002 |
| FR | 2 820 032 | 8/2002 |
| GB | 1026978 | 4/1966 |
| GB | 1153196 | 5/1969 |
| JP | 2-019576 | 1/1990 |
| JP | 10-508861 | 9/1998 |
| JP | 10-508862 | 9/1998 |
| JP | 10-316546 | 12/1998 |
| JP | 2001/206828 | 7/2001 |
| JP | 2001/220330 | 8/2001 |
| JP | 2002-509099 | 3/2002 |
| WO | WO94/08969 | 4/1994 |
| WO | WO94/08970 | 4/1994 |
| WO | WO96/15765 | 5/1996 |
| WO | WO96/15766 | 5/1996 |
| WO | WO98/03150 | 1/1998 |
| WO | WO98/44012 | 10/1998 |
| WO | WO99/11229 A | 3/1999 |
| WO | WO 00/68282 | 11/2000 |
| WO | WO 01/41717 | 6/2001 |
| WO | WO 01/78668 A | 10/2001 |
| WO | WO 02/00181 A1 | 1/2002 |
| WO | WO 02/22095 | 3/2002 |
| WO | WO 02/38116 A1 | 5/2002 |
| WO | WO 02/45673 A2 | 6/2002 |
| WO | WO 02/76923 | 10/2002 |
| WO | WO 02/96382 | 12/2002 |
| WO | WO 03/017956 | 3/2003 |

OTHER PUBLICATIONS

Office Action in Co-pending U.S. Appl. No. 10/834,349 dated Mar. 29, 2005 (Examiner Elhilo).
English language Derwent Abstract of DE 30 16 008 A1, Oct. 29, 1981.
English language Derwent Abstract of DE 201 18 982, Aug. 16, 2001.
English language Derwent Abstract of EP 0 770 375, May 2, 1997.
English language Derwent Abstract of JP 2-019576 (88-169571), Jan. 23, 1990.
French Search Report for FR 03 05243 Jan. 20, 2004, Examiner Vayassié.
French Search Report for FR 03 05241 Feb. 11, 2004, Examiner Voyiazoglou.
French Search Report for FR 03 05242 Feb. 12, 2004, Examiner Voyiazoglou.
G. Fonnum, J. Bakke and Fk. Hansen—Colloid Polym. Sci 271, 380-389 (1993).
English language Derwent Abstract of JP 10-508862, Sep. 2, 1998.
European Search Report for EP 04 291 086 (European counterpart to U.S. Appl. No. 10/834,270) dated Jul. 9, 2004, Examiner Voyiazoglou.
European Search Report for EP 04 291 095 (European counterpart to U.S. Appl. No. 10/834,349) dated Jul. 9, 2004, Examiner Voyiazoglou.

* cited by examiner

DYE COMPOSITION COMPRISING 2-CHLORO-6-METHYL-3-AMINOPHENOL AS COUPLER, PARA-AMINOPHENOL AND 3-METHYL-4-AMINOPHENOL AS OXIDATION BASES AND AT LEAST ONE ASSOCIATIVE THICKENING POLYMER

This application claims benefit of U.S. Provisional Application No. 60/507,120, filed Oct. 1, 2003.

The present disclosure relates to a composition for the oxidation dyeing of keratin fibers, for instance, human keratin fibers such as the hair, comprising 2-chloro-6-methyl-3-aminophenol as a coupler, at least one first oxidation base chosen from para-aminophenols, 3-methyl-4-aminophenol as the second oxidation base, and at least one associative thickening polymer.

It is known practice to dye keratin fibers, for instance, human keratin fibers such as the hair, with dye compositions containing oxidation dye precursors, which are generally known as oxidation bases, such as ortho- or para-phenylenediamines, ortho- or para-aminophenols and heterocyclic compounds. These oxidation bases are colorless or weakly colored compounds that, when combined with oxidizing products, can give rise to colored compounds by a process of oxidative condensation.

It is also known that the shades obtained with these oxidation bases may be varied by combining them with couplers or coloration modifiers, for example, coloration modifiers chosen from aromatic meta-diamines, meta-aminophenols, meta-diphenols and some heterocyclic compounds such as indole compounds.

The variety of molecules that may be used as oxidation bases and couplers allows a wide range of colors to be obtained.

The "permanent" coloration obtained with these oxidation dyes should, moreover, satisfy a certain number of requirements. For example, it should not have toxicological drawbacks, it should allow shades to be obtained in the desired intensity, and it should show good resistance to external agents such as light, bad weather, washing, permanent-waving, perspiration and rubbing.

The dyes should also allow white hairs to be covered and, finally, they should be as unselective as possible, i.e., they should be able to produce the smallest possible color differences along the same length of keratin fiber that may in fact be differently sensitized (i.e., damaged) between its end and its root.

Compositions for the oxidation dyeing of keratin fibers, comprising 2-chloro-6-methyl-3-aminophenol or 2-methyl-6-chloro-3-aminophenol as a coupler, in combination with oxidation bases conventionally used for oxidation dyeing, for instance select para-phenylenediamines or para-aminophenols, have been proposed, for example, in German Patent Application DE 30 16 008.

Patent Application WO 96/15766 describes compositions for the oxidation dyeing of keratin fibers, comprising the specific combination of 2-chloro-6-methyl-3-aminophenol as a coupler and a specific oxidation base chosen from para-aminophenol derivatives substituted in position 2 or 3, for instance 3-methyl-4-aminophenol, 2-allyl-4-aminophenol or 2-aminomethyl-4-aminophenol.

Compositions for the oxidation dyeing of keratin fibers, containing 2-chloro-6-methyl-3-aminophenol as a coupler, combined with at least two oxidation bases of different nature chosen from para-phenylenediamines, double bases, para-aminophenols, ortho-aminophenols and heterocyclic oxidation bases have also been proposed in the patent application EP 0 966 251.

However, such compositions are not entirely satisfactory, for example, with regards to the staying power of the colorations obtained with respect to the various attacking factors to which the hair may be subjected, for instance, with respect to shampoo, light, sweat and permanent-reshaping operations, and with regard to the strength of the colorations obtained.

Thus, it would be useful to provide novel compositions for the oxidation dyeing of keratin fibers that do not have the drawbacks of those dye compositions known in the art. For example, it would be useful to provide novel compositions that can produce strong, chromatic, aesthetic colorations in varied shades, which may show little selectivity and good resistance to the various attacking factors to which the hair may be subjected, such as shampoo, light, sweat and permanent-reshaping operations.

Accordingly, disclosed herein is a composition for the oxidation dyeing of keratin fibers, comprising, in a suitable dyeing medium:
  at least one coupler chosen from 2-chloro-6-methyl-3-aminophenol and the addition salts thereof;
  at least one first oxidation base chosen from para-aminophenols and the addition salts thereof;
  at least one second oxidation base chosen from 3-methyl-4-aminophenol, and the addition salts thereof; and
  at least one associative thickening polymer.

The composition according to the present disclosure, may allow a chromatic, very strong, sparingly selective and fast coloration of keratin fibers to be obtained.

Another embodiment of the present disclosure is a process for the oxidation dyeing of keratin fibers, for instance human keratin fibers such as the hair, using the composition disclosed herein.

The associative polymers that may be used according to the present disclosure are chosen from water-soluble and water-dispersible polymers capable, in an aqueous medium, of reversibly associating together or with other molecules. Their chemical structure comprises hydrophilic regions and hydrophobic regions characterized by at least one $C_8$-$C_{30}$ fatty chain, such as a $C_{10}$-$C_{30}$ fatty chain.

These polymers are derived from a free-radical polymerization or from a polycondensation, each starting with at least one monomer, at least one of which comprises a $C_8$-$C_{30}$, such as a $C_{10}$-$C_{30}$, fatty chain; alternatively, the polymers are derived from the grafting onto a polymer, for instance a polyhydroxylated polymer, of a compound comprising at least one $C_8$-$C_{30}$, such as a $C_{10}$-$C_{30}$, fatty chain.

As disclosed herein, the term "thickening polymer" means a polymer that has, for example, as a solution or a dispersion at 5% by weight of active material in water, a viscosity measured using a Rheomat RM 180 rheometer, at 25° C., of at least 500 cP, at a shear rate of 100 s$^{-1}$.

The associative polymers according to the present disclosure may be anionic, cationic, amphoteric or nonionic. For example, the associative polymers may be anionic, cationic or nonionic.

Among the associative polymers of anionic type that may be used, non-limiting mention may be made of:
  (I) associative polymers comprising at least one hydrophilic unit and at least one fatty-chain allyl ether unit, for instance, those whose hydrophilic unit comprises an ethylenic unsaturated anionic monomer, such as a vinylcarboxylic acid, for example, acrylic acid, methacrylic acid and mixtures thereof, wherein the fatty-chain allyl ether unit corresponds to the monomer of formula (V):

$$CH_2=CR'CH_2OB_nR \quad (V)$$

wherein:
R' is chosen from hydrogen atoms and $CH_3$ radicals;
B is an ethyleneoxy radical;
n is an integer ranging from zero to 100;
R is chosen from hydrocarbon-based radicals chosen from alkyl, arylalkyl, aryl, alkylaryl and cycloalkyl radicals, comprising from 8 to 30 carbon atoms, for instance 10 to 24 carbon atoms, such as from 12 to 18 carbon atoms.

For example, a unit of formula (V) may be a unit wherein R' is hydrogen, n is equal to 10 and R is a stearyl ($C_{18}$) radical.

Anionic associative polymers of this type are described and prepared, according to an emulsion polymerization process, in patent EP-0 216,479.

Among the anionic associative polymers that may be used according to the present disclosure, for example, are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (V), and from 0% to 1% by weight of at least one crosslinking agent that is a known copolymerizable unsaturated polyethylenic monomer, for instance diallyl phthalate, allyl (meth)acrylate, divinylbenzene, (poly)ethylene glycol dimethacrylate or methylenebisacrylamide.

Among the crosslinking polymers that may be used, further examples include crosslinked terpolymers of methacrylic acid, of ethyl acrylate and of polyethylene glycol (10 EO) stearyl ether (Steareth-10), for instance those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) associative polymers comprising at least one hydrophilic unit of unsaturated olefinic carboxylic acid type, and at least one hydrophobic unit of ($C_{10}$-$C_{30}$)alkyl ester of unsaturated carboxylic acid type.

For example, these polymers may be chosen from those in which the hydrophilic unit of unsaturated olefinic carboxylic acid type corresponds to the monomer of formula (VI):

(VI)

wherein $R_1$ is chosen from hydrogen atoms, and $CH_3$ and $C_2H_5$ radicals, i.e., acrylic acid, methacrylic acid or ethacrylic acid units, and from those in which the hydrophobic unit of ($C_{10}$-$C_{30}$)alkyl ester of unsaturated carboxylic acid type corresponds to the monomer of formula (VII):

(VII)

wherein:
$R_2$ is chosen from hydrogen atoms, and $CH_3$ and $C_2H_5$ radicals, i.e., acrylate, methacrylate or ethacrylate units,; for example H leads to acrylate units; $CH_3$ leads to methacrylate units;

$R_3$ is chosen from $C_{10}$-$C_{30}$ alkyl radicals, such as $C_{12}$-$C_{22}$ alkyl radicals.

($C_{10}$-$C_{30}$) alkyl esters of unsaturated carboxylic acids according to the present disclosure include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic associative polymers of this type are described and prepared, for example, in U.S. Pat. Nos. 3,915,921 and 4,509,949.

Further the anionic associative polymers of this type that may be used herein include polymers formed from a monomer mixture comprising:
  (i) essentially acrylic acid;
  (ii) an ester of formula (VII) described above in which $R_2$ is chosen from hydrogen atoms and $CH_3$ radicals, and $R_3$ is chosen from alkyl radicals comprising from 12 to 22 carbon atoms; and
  (iii) at least one crosslinking agent, which is a known copolymerizable polyethylenic unsaturated monomer, for instance diallyl phthalate, allyl (meth)acrylate, divinylbenzene, (poly)ethylene glycol dimethacrylate and methylenebisacrylamide.

Among the anionic associative polymers of this type that may be used, further non-limiting examples include those comprising from 60% to 95% by weight of acrylic acid (hydrophilic unit), from 4% to 40% by weight of $C_{10}$-$C_{30}$ alkyl acrylate (hydrophobic unit), and from 0% to 6% by weight of a crosslinking polymerizable monomer, or alternatively those comprising from 96% to 98% by weight of acrylic acid (hydrophilic unit), from 1% to 4% by weight of $C_{10}$-$C_{30}$ alkyl acrylate (hydrophobic unit), and from 0.1% to 0.6% by weight of a crosslinking polymerizable monomer such as those described above.

Among the polymers described above, which may be used according to the present disclosure, non-limiting examples include the products sold by the company Goodrich under the trade names Pemulen TR1®, Pemulen TR2® and Carbopol 1382®, and for example, Pemulen TR1®, as well as the product sold by the company SEPPIC under the name Coatex SX®.

(III) maleic anhydride/$C_{30}$-$C_{38}$ α-olefin/alkyl maleate terpolymers, such as the product, maleic anhydride/$C_{30}$-$C_{38}$ α-olefin/isopropyl maleate copolymer, sold under the name Performa V 1608® by the company Newphase Technologies.

(IV) acrylic terpolymers comprising:
  about 20% to 70% by weight of a carboxylic acid containing α,β-monoethylenic unsaturation;
  about 20% to 80% by weight of a non-surfactant monomer containing α,β-monoethylenic unsaturation, which is different than the carboxylic acid containing α,β-monoethylenic unsaturation;
  about 0.5% to 60% by weight of a nonionic monourethane which is the product of reaction of a monohydric surfactant with a monoisocyanate containing monoethylenic unsaturation; such as those described in the patent application EP-A-0 173,109, for instance, the terpolymer described in Example 3, which is a methacrylic acid/methyl acrylate/behenyl dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation, and an ester of a carboxylic acid containing α,β-monoethylenic unsaturation and of an oxyalkylenated fatty alcohol. For example, these compounds may also comprise as a monomer an ester of a carboxylic acid containing α,β-monoethylenic unsaturation and of a $C_1$-$C_4$ alcohol. A non-limiting example of a compound of this type which may be mentioned is Aculyn 22® sold by the company Rohm & Haas, which is a methacrylic acid/ethyl acrylate/stearyl methacrylate oxyalkylenated terpolymer.

(VI) and associative polyurethanes of anionic nature, such as Viscophobe DB 1000 from the company Union Carbide.

Among the associative polymers of cationic type, non-limiting mention may be made of:

(I) the cationic associative polyurethanes whose family has been described in French Patent Application 0 009,609, which may be chosen from polyurethanes of formula (VIII):

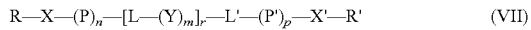

R—X—(P)$_n$—[L—(Y)$_m$]$_r$—L'—(P')$_p$—X'—R'    (VII)

wherein:
R and R', which may be identical or different, are chosen from hydrophobic groups and hydrogen atoms;
X and X', which may be identical or different, are chosen from groups comprising an amine function optionally bearing a hydrophobic group, or alternatively L" groups;
L, L' and L", which may be identical or different, are chosen from groups derived from a diisocyanate;
P and P', which may be identical or different, are chosen from groups comprising an amine function optionally bearing a hydrophobic group;
Y is chosen from hydrophilic groups;
r is an integer ranging from 1 to 100, for instance, from 1 to 50, such as from 1 to 25;
n, m and p each range, independently of each other, from 0 to 1000;

and wherein the molecule comprises at least one entity chosen from protonated and quaternized amine functional groups, and at least one hydrophobic group.

For example, in one embodiment of the polyurethanes of the present disclosure, the only hydrophobic groups are the groups R and R' at the chain ends.

Another non-limiting example of cationic associative polyurethanes that may be used includes those of formula (VIII) described above and wherein:
R and R' are each independently chosen from hydrophobic groups;
X and X' are each independently an L" group;
n and p range from 1 to 1000; and
L, L', L", P, P', Y and m have the meaning given above.

Further non-limiting examples of cationic associative polyurethanes that may be used include those of formula (VIII) above wherein:
R and R' are each independently chosen from hydrophobic groups;
X and X' are each independently an L" group;
n and p are each zero; and
L, L', L", Y and m have the meaning given above. When n and p are equal to zero, the polymers of formula (VIII) do not comprise units derived from a monomer comprising an amine function, incorporated into the polymer during the polycondensation. The protonated amine functions of these polyurethanes result from the hydrolysis of excess isocyanate functional groups, at the chain end, followed by alkylation of the primary amine functions formed with alkylating agents comprising a hydrophobic group, i.e., compounds of the type RQ or R'Q, wherein R and R' are as defined above and Q comprises a leaving group such as a halide, a sulphate, etc.

Yet another non-limiting example of cationic associative polyurethanes that may be used include those of formula (VIII) above wherein:
R and R' are each independently chosen from hydrophobic groups;
X and X' are each independently chosen from groups comprising a quaternary amine;
n and p are each zero; and
L, L', Y and m have the meaning given above.

The number-average molecular mass of the cationic associative polyurethanes may range from 400 to 500,000, for instance, from 1000 to 400,000, such as from 1000 to 300,000.

As used herein, the expression "hydrophobic group" means a radical or polymer comprising a saturated or unsaturated, linear or branched hydrocarbon-based chain, which may optionally comprise at least one hetero atom, such as phosphorus, oxygen, nitrogen or sulfur, or a radical comprising a perfluoro or silicone chain. When the hydrophobic group is chosen from hydrocarbon-based radicals, it comprises at least 10 carbon atoms, for instance from 10 to 30 carbon atoms, such as from 12 to 30 carbon atoms, and from 18 to 30 carbon atoms. For instance, the hydrocarbon-based group may be derived from a monofunctional compound.

By way of non-limiting example, the hydrophobic group may be derived from a fatty alcohol such as stearyl alcohol, dodecyl alcohol or decyl alcohol. It may also be chosen from hydrocarbon-based polymers such as, for example, polybutadiene.

When X and/or X' are chosen from groups comprising a tertiary or quaternary amine, X and X' may be chosen from at least one of the following formulae:

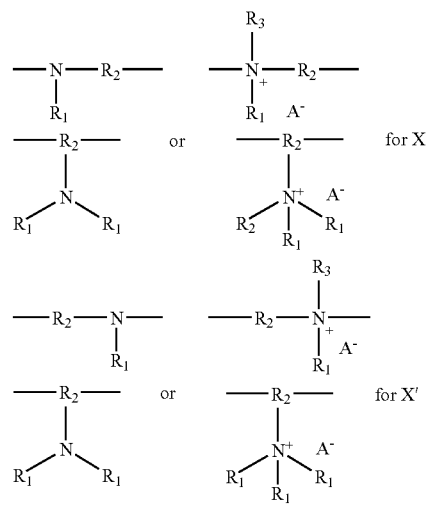

wherein:
$R_2$ is chosen from linear and branched alkylene radicals comprising from 1 to 20 carbon atoms optionally comprising an entity chosen from saturated and unsaturated rings, and arylene radicals, wherein at least one of the carbon atoms may be replaced with a hetero atom chosen from nitrogen, sulfur, oxygen and phosphorus;

$R_1$ and $R_3$, which may be identical or different, are chosen from linear and branched $C_1$-$C_{30}$ alkyl and alkenyl radicals and aryl radicals, wherein at least one of the carbon atoms may be replaced with a hetero atom chosen from nitrogen, sulfur, oxygen and phosphorus;

$A^-$ is a physiologically acceptable counter-ion.

The groups L, L' and L", derived from groups derived from a diisocyanate, are chosen from groups of formula:

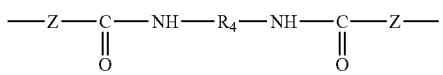

wherein:

Z is chosen from oxygen and sulfur atoms, and —NH— radicals; and $R_4$ is chosen from linear and branched alkylene radicals comprising from 1 to 20 carbon atoms optionally comprising an entity chosen from saturated and unsaturated rings, and arylene radicals, wherein at least one of the carbon atoms may be replaced with a hetero atom chosen from nitrogen, sulfur, oxygen, and phosphorus atoms.

The groups P and P' comprising an amine functional group as defined above, may be chosen from at least one of the following formulae:

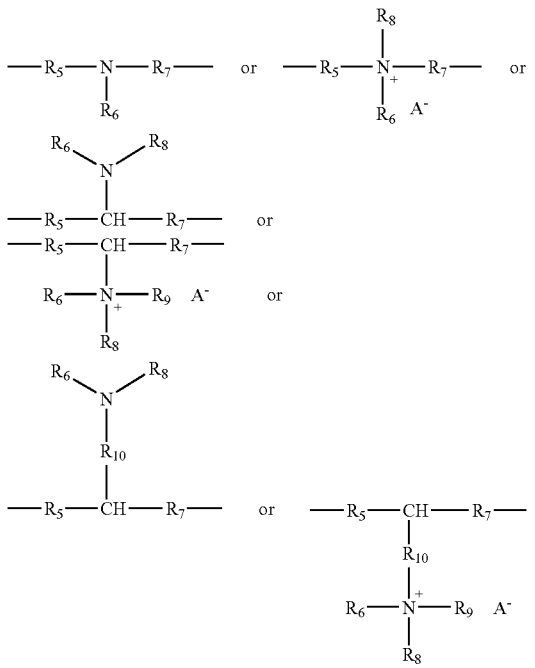

wherein:

$R_5$ and $R_7$, which may be identical or different, are chosen from linear and branched alkylene radicals comprising from 1 to 20 carbon atoms, optionally comprising an entity chosen from saturated and unsaturated rings, and arylene radicals, wherein at least one of the carbon atoms may be replaced with a hetero atom chosen from nitrogen, sulfur, oxygen and phosphorus;

$R_6$, $R_8$ and $R_9$, which may be identical or different, are chosen from linear and branched $C_1$-$C_{30}$ alkyl and alkenyl radicals and aryl radicals, wherein at least one of the carbon atoms may be replaced with a hetero atom chosen from nitrogen, sulfur, oxygen and phosphorus;

$R_{10}$ is chosen from linear and branched, optionally unsaturated, alkylene groups which may comprise at least one hetero atom chosen from nitrogen, oxygen, sulfur, and phosphorus atoms; and $A^-$ is a physiologically acceptable counter-ion.

As used herein, the term "hydrophilic group" means a polymeric or non-polymeric water-soluble group.

By way of example, when the hydrophilic group is not a polymer, non-limiting mention may be made of ethylene glycol, diethylene glycol and propylene glycol.

When the hydrophilic group is a hydrophilic polymer, in accordance with one aspect of the present disclosure, non-limiting mention may be made, for example, of polyethers, sulphonated polyesters, sulphonated polyamides or a mixture of these polymers. The hydrophilic group, may be, for example, a polyether, such as poly(ethylene oxide) or poly (propylene oxide).

The cationic associative polyurethanes of formula (VIII) according to the present disclosure are formed from diisocyanates and from various compounds with functional groups comprising labile hydrogen. The functional groups comprising labile hydrogen may include alcohol, primary and secondary amine, and thiol functions giving, after reaction with the diisocyanate functional groups, polyurethanes, polyureas and polythioureas, respectively. The term "polyurethanes" as used in the present disclosure encompasses these three types of polymers, namely polyurethanes per se, polyureas and polythioureas, and also copolymers thereof.

A first type of compound involved in the preparation of the polyurethane of formula (VIII) is a compound comprising at least one unit comprising an amine functional group. This compound may be multifunctional, or, for example, difunctional. According to one aspect of the present disclosure, this compound may comprise two labile hydrogen atoms borne, for example, by a hydroxyl, primary amine, secondary amine or thiol functional group. A mixture of multifunctional and difunctional compounds wherein the percentage of multifunctional compounds is low may also be used.

As mentioned above, this compound may comprise more than one unit comprising an amine function. If this is the case, it is a polymer bearing a repetition of the unit comprising an amine function. Compounds of this type may be chosen from those of the following formulae:

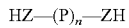

and

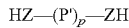

wherein Z, P, P', n and p are as defined above.

Non-limiting examples of compounds comprising an amine function that may be used include N-methyldiethanolamine, N-tert-butyldiethanolamine and N-sulphoethyldiethanolamine.

The second compound involved in the preparation of the polyurethane of formula (VIII) is a diisocyanate of formula:

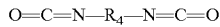

wherein $R_4$ is as defined above. By way of example, non-limiting mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (VIII) is a hydrophobic compound intended to form the terminal hydrophobic groups of the polymer of formula (VIII). This compound comprises a hydrophobic group and a functional group comprising a labile hydrogen, for example a hydroxyl, primary or secondary amine, or thiol function. By way of non-limiting example, this compound may be chosen from fatty alcohols such as, for instance, stearyl alcohol, dodecyl alcohol or decyl alcohol. When this compound comprises a polymeric chain, it may be, for example, a-hydroxylated hydrogenated polybutadiene.

The hydrophobic group of the polyurethane of formula (VIII) may also result from the quaternization reaction of the tertiary amine of the compound comprising at least one tertiary amine unit. In this case, the hydrophobic group is introduced via the quaternizing agent. The quaternizing agent is a compound chosen from RQ and R'Q, as defined above.

The cationic associative polyurethane may also comprise a hydrophilic block. This block is provided by a fourth type of compound involved in the preparation of the polymer. This compound may be multifunctional, and, for example it may be difunctional. It is also possible to have a mixture wherein the percentage of multifunctional compound is low. The functional groups comprising labile hydrogens are alcohol, primary or secondary amine or thiol functional groups. This compound may be a polymer terminated at the chain ends with one of these functional groups comprising a labile hydrogen.

By way of example, when the compound is not a polymer, non-limiting mention may be made of ethylene glycol, diethylene glycol and propylene glycol. When the compound is a hydrophilic polymer, non-limiting mention may be made, for example, of polyethers, sulphonated polyesters and sulphonated polyamides, or a mixture of these polymers. The hydrophilic compound may be, for instance, a polyether, such as poly(ethylene oxide) or poly(propylene oxide).

The hydrophilic group termed Y in formula (VIII) is optional, as the units comprising a quaternary amine or protonated functional group may suffice to provide the solubility or water-dispersibility required for this type of polymer in an aqueous solution.

Although the presence of a hydrophilic group Y is optional, cationic associative polyurethanes comprising such a group are, for example, used in one embodiment of the composition disclosed herein.

(II) quaternized cellulose derivatives and polyacrylates comprising non-cyclic amine side groups.

Among the quaternized cellulose derivatives that may be used, non-limiting mention may be made of:
  quaternized celluloses modified with groups comprising at least one fatty chain, such as alkyl, arylalkyl or alkylaryl groups comprising at least 8 carbon atoms, or mixtures thereof;
  quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses may comprise for example, from 8 to 30 carbon atoms. The aryl radicals, for instance, may be chosen from phenyl, benzyl, naphthyl and anthryl groups.

Non-limiting examples of quaternized alkylhydroxyethylcelluloses comprising $C_8$-$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol and the products Crodacel QM®, Crodacel QL® ($C_{12}$ alkyl) and Crodacel QS® ($C_{18}$ alkyl) sold by the company Croda.

(III) and cationic polyvinyllactams, the family of which was described by L'Oréal in the French Patent Application FR 0 101,106. Such polymers comprise:

(a) at least one monomer chosen from vinyllactams and alkylvinyllactams;

(b) at least one monomer chosen from those of formulae (IX) and (X):

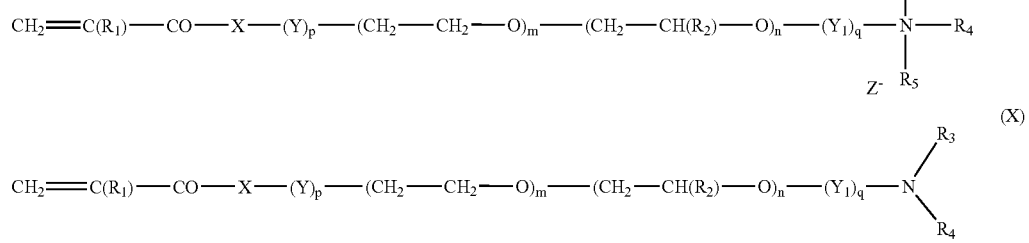

wherein:
  X is chosen from oxygen atoms and $NR_6$ radicals;
  $R_1$ and $R_6$, which may be identical or different, are chosen from hydrogen atoms, and linear and branched $C_1$-$C_5$ alkyl radicals;
  $R_2$ is chosen from linear and branched $C_1$-$C_4$ alkyl radicals;
  $R_3$, $R_4$ and $R_5$, which may be identical or different, are chosen from hydrogen atoms, linear and branched $C_1$-$C_{30}$ alkyl radicals, and radicals of formula (XI):

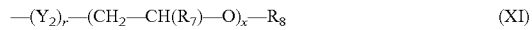

wherein:
  Y, $Y_1$ and $Y_2$, which may be identical or different, are chosen from linear and branched $C_2$-$C_{16}$ alkylene radicals;

$R_7$ is chosen from hydrogen atoms, linear and branched $C_1$-$C_4$ alkyl radicals, and linear and branched $C_1$-$C_4$ hydroxyalkyl radicals;

$R_8$ is chosen from hydrogen atoms and linear and branched $C_1$-$C_{30}$ alkyl radicals;

p, q and r, which may be identical or different, are integers equal to the value 0 and the value 1;

m and n, which may be identical or different, are integers ranging from 0 to 100;

x is an integer ranging from 1 to 100;

$Z^-$ is chosen from organic and mineral acid anions, with the proviso that:

at least one of the substituents $R_3$, $R_4$, $R_5$ or $R_8$ is chosen from linear and branched $C_9$-$C_{30}$ alkyl radicals;

if m or n is not zero, then q is equal to 1; and if m or n is equal to zero, then p or q is equal to 0.

The cationic poly(vinyllactam) polymers according to the present disclosure may be crosslinked or non-crosslinked and may also be block polymers.

The counter-ion $Z^-$ of the monomers of formula (IX), for instance, may be chosen from halide ions, phosphate ions, the methosulphate ion and the tosylate ion.

For example, $R_3$, $R_4$ and $R_5$, which may be identical or different, may be chosen from hydrogen atoms and linear and branched $C_1$-$C_{30}$ alkyl radicals.

For further example, the monomer (b) may be chosen from monomers of formula (IX), such as wherein m and n are equal to zero.

The vinyllactam or alkylvinyllactam monomer may be, for example, chosen from those of formula (XII):

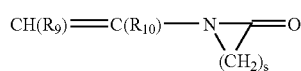

(XII)

wherein:

s is an integer ranging from 3 to 6;

$R_9$ is chosen from hydrogen atoms and $C_1$-$C_5$ alkyl radicals;

$R_{10}$ is chosen from hydrogen atoms and $C_1$-$C_5$ alkyl radicals;

with the proviso that at least one of the radicals $R_9$ and $R_{10}$ is a hydrogen atom.

For example, the monomer (XII) may be vinylpyrrolidone.

The cationic poly(vinyllactam) polymers according to the present disclosure may also comprise at least one additional monomer, such as cationic or nonionic monomers.

Among compounds that may be used according to the present disclosure, non-limiting mention may be made of terpolymers comprising:

(a) at least one monomer of formula (XII);

(b) at least one monomer of formula (IX) wherein p=1, q=0, $R_3$ and $R_4$, which may be identical or different, are chosen from hydrogen atoms and $C_1$-$C_5$ alkyl radicals, and $R_5$ is chosen from $C_9$-$C_{24}$ alkyl radicals; and (c) at least one monomer of formula (X) wherein $R_3$ and $R_4$, which may be identical or different, are chosen from hydrogen atoms and $C_1$-$C_5$ alkyl radicals. For further example, terpolymers comprising, by weight, 40% to 95% of monomer (a), 0.1% to 55% of monomer (c), and 0.25% to 50% of monomer (b) may be used.

Such polymers are described in the patent application WO 00/68282, the disclosure of which is hereby incorporated by reference.

Among cationic poly(vinyllactam) polymers according to the disclosure, vinylpyrrolidone/dimethylaminopropylmethacrylamide/dodecyldimethylmethacryl-amidopropylammonium tosylate terpolymers, vinyl-pyrrolidone/dimethylaminopropylmethacrylamide/cocoyl-dimethylmethacrylamidopropylammonium tosylate terpolymers, and vinylpyrrolidone/dimethylaminopropylmethacrylamide/lauryldimethylmethacrylamidopropyl-ammonium tosylate or chloride terpolymers are non-limiting examples of polymers that may be used.

The weight-average molecular mass of the cationic poly (vinyllactam) polymers according to the present disclosure may range, for instance, from 500 to 20,000,000. For example, it may range from 200,000 to 2,000,000, and from 400,000 to 800,000.

The amphoteric associative polymers that may be used, for instance, may be chosen from polymers comprising at least one non-cyclic cationic unit. For further example, those prepared from or comprising from 1 to 20 mol % of a monomer comprising a fatty chain, such as from 1.5 to 15 mol % and from 1.5 to 6 mol %, relative to the total number of moles of monomers, may be used.

Non-limiting examples of the amphoteric associative polymers that may be used according to the present disclosure comprise, or are prepared by copolymerizing:

1) at least one monomer chosen from those of formulae (XIII) and (XIV):

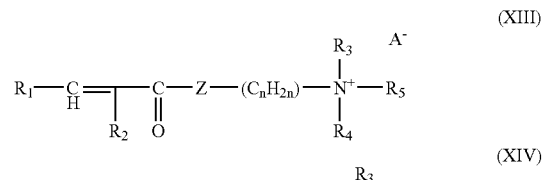

wherein:

$R_1$ and $R_2$, which may be identical or different, are chosen from hydrogen atoms and methyl radicals;

$R_3$, $R_4$ and $R_5$, which may be identical or different, are chosen from linear and branched alkyl radicals comprising from 1 to 30 carbon atoms;

Z is chosen from NH groups and oxygen atoms;

n is an integer from 2 to 5;

$A^-$ is an anion derived from organic and mineral acids, such as methosulphate anions or halides such as chloride or bromide;

2) at least one monomer of formula (XV):

$R_6$—CH=$CR_7$—COOH        (XV)

wherein:

$R_6$ and $R_7$, which may be identical or different, are chosen from hydrogen atoms and methyl radicals; and 3) at least one monomer of formula (XVI):

$R_6$—CH=$CR_7$—$COXR_8$        (XVI)

wherein:

$R_6$ and $R_7$, which may be identical or different, are chosen from hydrogen atoms and methyl radicals;

X is chosen from oxygen and nitrogen atoms; and $R_8$ is chosen from linear and branched alkyl radicals comprising from 1 to 30 carbon atoms;

and wherein at least one of the monomers of formulae (XIII), (XIV) and (XV) comprises at least one fatty chain.

The monomers of formulae (XIII) and (XIV) of the present disclosure may be chosen from, for example:
dimethylaminoethyl methacrylate, dimethylaminoethyl acrylate;
diethylaminoethyl methacrylate, diethylaminoethyl acrylate;
dimethylaminopropyl methacrylate, dimethylaminopropyl acrylate;
dimethylaminopropylmethacrylamide, dimethylaminopropylacrylamide;

wherein these monomers may optionally be quaternized, for example with a $C_1$-$C_4$ alkyl halide or a $C_1$-$C_4$ dialkyl sulphate. For example, the at least one monomer of formula (XIII) may be chosen from acrylamidopropyltrimethylammonium chloride and methacrylamidopropyltrimethylammonium chloride.

The at least one monomer of formula (XIV) of the present disclosure may be, for example, chosen from acrylic acid, methacrylic acid, crotonic acid and 2-methylcrotonic acid. For instance, the at least one monomer of formula (XIV) may be acrylic acid. The at least one monomer of formula (XIV) of the present disclosure may be, for instance, chosen from $C_{12}$-$C_{22}$, such as $C_{16}$-$C_{18}$ alkyl acrylates and methacrylates.

The monomers constituting the fatty-chain amphoteric polymers as disclosed herein may be, for example, neutralized and/or quaternized.

The ratio of the number of cationic charges/anionic charges may be, for instance, equal to about 1.

The amphoteric associative polymers according to the present disclosure may, for example, comprise from 1 to 10 mol %, such as from 1.5 to 6 mol %, of the at least one monomer comprising a fatty chain, i.e., at least one monomer of formulae (XIII), (XIV) and (XV)).

The weight-average molecular weights of the amphoteric associative polymers according to the present disclosure may range from 500 to 50,000,000, such as from 10,000 to 5,000,000.

The amphoteric associative polymers according to the present disclosure may also comprise other monomers such as nonionic monomers and, for instance, such as $C_1$-$C_4$ alkyl acrylates or methacrylates. Amphoteric associative polymers according to the present disclosure are described and prepared, for example, in the Patent Application WO 98/44012.

Among the amphoteric associative polymers according to the present disclosure, non-limiting mention may be made of acrylic acid/(meth)acrylamidopropyl-trimethylammonium chloride/stearyl methacrylate terpolymers.

According to the present disclosure, the nonionic associative polymers may be chosen from:
(1) celluloses modified with groups comprising at least one fatty chain;

non-limiting examples that may be mentioned include:
hydroxyethylcelluloses modified with groups comprising at least one fatty chain, such as alkyl, arylalkyl or alkylaryl groups, or mixtures thereof, and in which the alkyl groups range from $C_8$-$C_{22}$, for instance the product Natrosol Plus Grade 330 CS® ($C_{16}$ alkyls) sold by the. company Aqualon, or the product Bermocoll EHM 100® sold by the company Berol Nobel,
polymers modified with alkylphenyl polyalkylene glycol ether groups, such as the product Amercell Polymer HM-1500® (nonylphenyl polyethylene glycol (15) ether) sold by the company Amerchol;
(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc;
(3) copolymers of vinylpyrrolidone and of fatty-chain hydrophobic monomers; non-limiting examples that may be mentioned include:
the products Antaron V216® or Ganex V216® (vinylpyrrolidone/hexadecene copolymer) sold by the company I.S.P.,
the products Antaron V220® or Ganex V220® (vinylpyrrolidone/eicosene copolymer) sold by the company I.S.P.;
(4) copolymers of $C_1$-$C_6$ alkyl methacrylates and acrylates and of amphiphilic monomers comprising at least one fatty chain, such as, for example, the oxyethylenated methyl acrylate/stearyl acrylate copolymer sold by the company Goldschmidt under the name Antil 208®;
(5) copolymers of hydrophilic methacrylates and acrylates and of hydrophobic monomers comprising at least one fatty chain, such as, for example, the polyethylene glycol methacrylate/lauryl methacrylate copolymer;
(6) polyurethane polyethers comprising in their chain both hydrophilic blocks, usually of polyoxyethylenated nature, and hydrophobic blocks which may be aliphatic sequences alone and/or cycloaliphatic and/or aromatic sequences;
(7) polymers with an aminoplast ether skeleton comprising at least one fatty chain, such as the Pure Thix® compounds sold by the company Sud-Chemie.

For example, the polyurethane polyethers may comprise at least two hydrocarbon-based lipophilic chains comprising from 6 to 30 carbon atoms, separated by a hydrophilic block, wherein the hydrocarbon-based chains may be pendent chains, or chains at the end of the hydrophilic block. For instance, it is possible for at least one pendent chain to be included. In addition, the polymer may comprise a hydrocarbon-based chain at one end or at both ends of a hydrophilic block.

The polyurethane polyethers may be multiblock, for instance, in triblock form. Hydrophobic blocks may be at each end of the chain, for example: triblock copolymers with a hydrophilic central block, or distributed both at the ends and in the chain, for example, multiblock copolymer. These same polymers may also be graft polymers or starburst polymers.

The nonionic fatty-chain polyurethane polyethers may be triblock copolymers wherein the hydrophilic block is a polyoxyethylenated chain comprising from 50 to 1000 oxyethylene groups. The nonionic polyurethane polyethers comprise a urethane linkage between the hydrophilic blocks, whence arises the name. By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used according to the present disclosure, non-limiting mention may also be made of Rheolate 205® comprising a urea function, sold by the company Rheox, or the Rheolates® 208, 204 or 212, and also Acrysol RM 184®. Non-limiting mention may also be made of the product Elfacos T210® comprising a $C_{12-14}$ alkyl chain, and the, product Elfacos T212® comprising a $C_{18}$ alkyl chain, from Akzo. The product DW 1206B® from Rohm & Haas comprising a $C_{20}$ alkyl chain and a urethane linkage, sold at a solids content of 20% in water, may also be used.

It is also possible to use solutions or dispersions of these polymers, such as in water or in aqueous-alcoholic medium. Non-limiting examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the present disclosure, for instance, include those described in the article by G. Fonnum, J. Bakke and Fk. Hansen—Colloid Polym. Sci 271, 380-389 (1993).

For further example, according to the present disclosure, it is possible to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold, for instance, by the company Rohm & Haas under the names Aculyn 46® and Aculyn 44®. Aculyn 46® is a polycondensate of polyethylene glycol containing 150 to 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 to 180 mol of ethylene oxide, of decyl alcohol and of methylenebis(4-cyclohexylisocyanate) (SMDI), at 35% by weight in a mixture of propylene glycol (39%) and water (26%).

In one embodiment of the present disclosure, the associative polymers may be chosen from nonionic and cationic associative polymers, such as polyether polyurethanes comprising hydrophilic and hydrophobic blocks; polymers comprising an aminoplast ether skeleton comprising at least one fatty chain; cationic associative polyurethanes; quaternized cellulose derivatives comprising at least one fatty chain; and cationic polyvinyllactams.

In another embodiment of the present disclosure, the associative polymer may be chosen from quaternized ($C_8$-$C_{30}$)alkylhydroxyethylcelluloses, such as laurylhydroxyethylcellulose.

The nonionic, anionic, cationic or amphoteric associative polymers may be used, for example, in an amount that may range from about 0.01% to 10% by weight, relative to the total weight of the dye composition. For instance, this amount may range from about 0.1% to 5% by weight, such as from about 0.5% to 3% by weight.

The composition according to the present disclosure may additionally comprise at least one additional oxidation base chosen from oxidation bases conventionally used in oxidation dyeing other than para-aminophenol and 3-methyl-4-aminophenol. By way of non-limiting example these additional oxidation bases may be chosen from para-phenylenediamines; bisphenylalkylenediamines; para-aminophenols other than para-aminophenol and 3-methyl-4-aminophenol; ortho-aminophenols; heterocyclic bases; and the addition salts thereof.

Among the para-phenylenediamines that may be used, non-limiting mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl-para-phenylenediamine, 4-amino-N,N-bis(β-hydroxyethyl)-2-methylaniline, 4-amino-N,N-bis(β-hydroxyethyl)-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxy-ethyloxy)-para-phenylenediamine, 2-(β-acetylaminoethyloxy)-para-phenylenediamine, N-(β-methoxyethyl)-para-phenylenediamine, 2-thienyl-para-phenylenediamine, 2-(β-hydroxyethyl)amino-5-aminotoluene, and the addition salts thereof.

Further among the para-phenylenediamines listed above, non-limiting mention may be made of para-phenylenediamine, para-tolylenediamine, 2-isopropyl-para-phenylenediamine, 2-(β-hydroxyethyl)-para-phenylenediamine, 2-(β-hydroxyethyl)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl-para-phenylenediamine, 2-chloro-para-phenylenediamine, 2-(β-acetylaminoethyloxy)-para-phenylenediamine, and the addition salts thereof.

Among the bisphenylalkylenediamines that may be used, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4'-aminophenyl) tetramethylenediamine, N,N'-bis(β-hydroxyethyl)-N,N'-bis(4'-aminophenyl)tetramethylenediamine, N,N'-bis(4'-methylaminophenyl)-tetramethylenediamine, N,N'-bis(ethyl)-N,N'-bis(4'-amino-3'-methylphenyl) ethylenediamine, 1,8-bis(2,5-diaminophenoxy)-3,6-dioxaoctane, and the addition salts thereof.

Among the para-aminophenols other than para-aminophenol and 3-amino-4-methylphenol, non-limiting mention may be made of, for example, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2-chlorophenol 4-amino-6-[(5'-amino-2'-hydroxy-3'-methylphenyl)methyl]-2-methylphenol, bis(5-amino-2-hydroxyphenyl)methane, 4-amino-2,6-dichlorophenol, and the addition salts thereof.

Among the ortho-aminophenols that may be used, non-limiting mention may be made, for example, of 2-aminophenol, 2-amino-5-methylphenol, 2-amino-6-methylphenol, 5-acetamido-2-aminophenol, and the addition salts thereof.

Among the heterocyclic bases that may be used, non-limiting mention may be made, for example, of pyridine derivatives, pyrimidine derivatives and pyrazole derivatives.

Among the pyridine derivatives that may be used, non-limiting mention may be maed of the compounds described, for example, in the patents GB 1,026,978 and GB 1,153,196, as well as 2,5-diaminopyridine, 2-(4-methoxyphenyl) amino-3-aminopyridine, 2,3-diamino-6-methoxypyridine, 2-(β-methoxyethyl)amino-3-amino-6-methoxypyridine, 3,4-diaminopyridine, and the addition salts thereof.

Other pyridine oxidation bases that may be useful according to the present disclosure include the 3-aminopyrazolo

[1,5-a]pyridine oxidation bases and the addition salts thereof described, for example, in the patent application FR 2,801, 308. By way of example, non-limiting mention may be made of pyrazolo[1,5-a]pyrid-3-ylamine; 2-acetylaminopyrazolo [1,5-a]pyrid-3-ylamine; 2-morpholin-4-ylpyrazolo[1,5-a] pyrid-3-ylamine; 3-aminopyrazolo[1,5-a]pyridine-2-carboxylic acid; 2-methoxypyrazolo[1,5-a]pyrid-3-ylamino; (3-aminopyrazolo[1,5-a]pyrid-7-yl)methanol; 2-(3-aminopyrazolo[1,5-a]pyrid-5-yl)ethanol; 2-(3-aminopyrazolo [1,5-a]pyrid-7-yl)ethanol; (3-aminopyrazolo[1,5-a]pyrid-2-yl)-methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino] ethanol; 2-[(3-aminopyrazolo-[1,5-a]pyrid-7-yl)(2-hydroxyethyl)amino]ethanol; 3-aminopyrazolo-[1,5-a]pyrid-5-ol; 3-aminopyrazolo[1,5-a]pyrid-4-ol; 3-aminopyrazolo[1,5-a] pyrid-6-ol; 3-aminopyrazolo[1,5-a]pyrid-7-ol, and also the addition salts thereof.

Among the pyrimidine derivatives that may be used, non-limiting mention may be made of the compounds described, for example, in German Patent No. DE 23 59,399 or Japanese Patent Nos. JP 88-169571 and JP 05-63124; European Patent No. EP 0 770,375, or patent application WO 96/15765, such as 2,4,5,6-tetraaminopyrimidine; 4-hydroxy-2,5,6-triaminopyrimidine; 2-hydroxy-4,5,6-triaminopyrimidine; 2,4-dihydroxy-5,6-diaminopyrimidine; 2,5,6-triaminopyrimidine; the addition salts thereof and the tautomeric forms thereof, when a tautomeric equilibrium exists.

Among the pyrazole derivatives that may be used, non-limiting mention may be made of the compounds described in German Patent Nos. DE 38 43,892 and DE 41 33,957, and patent applications WO 94/08969, WO 94/08970, FR-A-2, 733,749 and DE 195 43,988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-ethyl-3-methyl pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole; 3,5-diamino-4-(β-hydroxyethyl) amino-1-methylpyrazole, and the addition salts thereof.

For example, the composition of the invention may comprise as the only oxidation bases:
at least one first oxidation base chosen from para-aminophenol and the addition salts thereof; and
at least one second oxidation base chosen from 3-methyl-4-aminophenol and the addition salts thereof.

Each oxidation base present in the composition as disclosed herein may be present in an amount ranging from 0.001% to 10%, such as from 0.005% to 6% by weight, relative to the total weight of the dye composition.

The composition according to the present disclosure may comprise, in addition to the 2-chloro-6-methyl-3-aminophenol, at least one additional coupler chosen from couplers conventionally used for the oxidation dyeing of keratin fibers. Among such couplers that may be used, non-limiting mention may be made of meta-phenylenediamines, meta-aminophenols other than 2-chloro-6-methyl-3-aminophenol, meta-diphenols, naphthalene-based couplers, heterocyclic couplers, and the addition salts thereof.

Further non-limiting examples that may be mentioned include 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2, 6-dimethoxypyridine, 1-N-(β-hydroxyethyl)-amino-3,4-methylenedioxybenzene, 2,6-bis(β-hydroxyethylamino) toluene, and the addition salts thereof.

For example, the composition as disclosed herein may comprise as the sole coupler at least one coupler chosen from 2-chloro-6-methyl-3-aminophenol and the addition salts thereof.

In the composition according to the present disclosure, each coupler may be present in an amount ranging from 0.001% to 10% by weight, such as from 0.005% to 6%, relative to the total weight of the dye composition.

In general, the addition salts of the oxidation bases and of the couplers that may be used in the context of the invention may be chosen, for example, from the addition salts with an acid, such as the hydrochlorides, hydrobromides, sulphates, citrates, succinates, tartrates, lactates, tosylates, benzenesulphonates, phosphates and acetates; and the addition salts with a base, such as sodium hydroxide, potassium hydroxide, aqueous ammonia, amines and alkanolamines.

The dye composition in accordance with the present disclosure may also comprise at least one direct dye that may be chosen from, for example nitrobenzene dyes, azo direct dyes and methine direct dyes. These direct dyes may be chosen from nonionic, anionic and cationic direct dyes.

The medium that is suitable for dyeing, also known as a dye support, generally comprises water, or a mixture of water and at least one organic solvent in order to dissolve the compounds that would not be sufficiently soluble in the water. Non-limiting examples of organic solvents that may be mentioned include $C_1$-$C_4$ lower alkanols, such as ethanol and isopropanol; polyols and polyol ethers, for instance 2-butoxyethanol; propylene glycol; propylene glycol monomethyl ether; diethylene glycol monoethyl ether; monomethyl ether; and also aromatic alcohols, for instance benzyl alcohol, phenoxyethanol, and mixtures thereof.

The solvents may be present in an amount ranging from 1% to 40% by weight, such as from 5% to 30% by weight, relative to the total weight of the dye composition.

The dye composition in accordance with the present disclosure may also comprise various adjuvants conventionally used in hair dye compositions, such as anionic, cationic, nonionic, amphoteric and zwitterionic surfactants, and mixtures thereof; anionic, cationic, nonionic, amphoteric and zwitterionic polymers, and mixtures thereof; mineral and organic thickeners, for instance anionic, cationic, nonionic and amphoteric associative thickening polymers; antioxidants; penetrating agents; sequestering agents; fragrances; buffers; dispersants; conditioners, for instance volatile or non-volatile, modified or unmodified silicones; film-forming agents; ceramides; preserving agents; and opacifiers.

The above adjuvants may be present in an amount for each ranging from 0.001% to 20% by weight, relative to the weight of the composition.

Needless to say, a person skilled in the art will take care to select any of the additional optional compounds such that the advantageous properties intrinsically associated with the oxidation dye composition in accordance with the present disclosure are not, or are not substantially, adversely affected by the envisaged addition(s).

The pH of the dye composition as disclosed herein may range from 3 to 12, such as from 5 to 11. It may be adjusted to the desired value by means of acidifying or basifying agents usually used for dyeing keratin fibers, or alternatively using standard buffer systems.

Among the acidifying agents that may be used, non-limiting mention may be made, for example, of mineral and organic acids, for instance hydrochloric acid, orthophosphoric acid, sulphuric acid, carboxylic acids such as acetic acid, tartaric acid, citric acid or lactic acid, and sulphonic acids.

Among the basifying agents that may be used, non-limiting mention may be made, for example, of aqueous ammonia, alkaline carbonates, alkanolamines such as mono-ethanolamine, diethanolamine and triethanolamine and derivatives thereof, sodium hydroxide, potassium hydroxide and the compounds of formula (I) below:

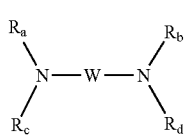

(I)

wherein W is a propylene residue optionally substituted with an entity chosen from hydroxyl groups and $C_1$-$C_4$ alkyl radicals; $R_a$, $R_b$, $R_c$ and $R_d$, which may be identical or different, may be chosen from hydrogen atoms, and $C_1$-$C_4$ alkyl and $C_1$-$C_4$ hydroxyalkyl radicals.

The dye composition according to the present disclosure may be in various forms, such as in the form of liquids, creams or gels, or in any other form that is suitable for dyeing keratin fibers, such as human hair.

The process as disclosed herein is a process in which a composition as defined above is applied to the keratin fibers, and the color is developed using an oxidizing agent. The color may be revealed at acidic, neutral or alkaline pH and the oxidizing agent may be added to the composition of the invention just at the time of use, or it may be introduced using an oxidizing composition comprising it, applied simultaneously with, or sequentially to, the composition of the invention.

According to one embodiment of the present disclosure, the composition as disclosed herein is mixed, for instance at the time of use, with a composition comprising, in a medium that is suitable for dyeing, at least one oxidizing agent, said oxidizing agent being present in an amount that is sufficient to develop a coloration. The mixture obtained is then applied to the keratin fibers. After a leave-in time ranging from 3 to 50 minutes, such as from 5 to 30 minutes, the keratin fibers are rinsed, washed with shampoo, rinsed again and then dried.

The oxidizing agents conventionally used for the oxidation dyeing of keratin fibers are, include, for example, hydrogen peroxide, urea peroxide, alkali metal bromates, persalts such as perborates and persulphates, peracids, and oxidase enzymes, among which non-limiting mention may be made of peroxidases, 2-electron oxidoreductases such as uricases, and 4-electron oxygenases, for instance laccases. In one embodiment of the present disclosure, hydrogen peroxide is used.

The oxidizing composition may also comprise various adjuvants conventionally used in hair dye compositions and as defined above. The pH of the oxidizing composition comprising the oxidizing agent is such that, after mixing with the dye composition, the pH of the resulting composition applied to the keratin fibers ranges for example, from 3 to 12, such as from 5 to 11. The pH may be adjusted to the desired value by means of acidifying or basifying agents usually used in the dyeing of keratin fibers and as defined above.

The ready-to-use composition that is applied to the keratin fibers may be in various forms, such as in the form of liquids, creams or gels, or in any other form that is suitable for dyeing keratin fibers, for instance human hair.

Another aspect of the present disclosure is also a multi-compartment device or "kit" for dyeing, wherein at least one first compartment comprises the dye composition as disclosed herein, and at least one second compartment comprises an oxidizing composition. This device may be equipped with a means for applying the desired mixture to the hair, such as the devices described in Patent FR 2,586, 913. Using this device, it is possible to dye keratin fibers using a process that involves mixing a dye composition as disclosed herein with an oxidizing agent as defined above, and applying the mixture obtained to the keratin fibers for a time that is sufficient to develop the desired coloration.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The following example is intended to illustrate the invention without limiting the scope as a result.

EXAMPLE

A dye composition was prepared as indicated below:

| Example 1 | |
|---|---|
| 2-Chloro-6-methyl-3-aminophenol | 1.37 g |
| para-Aminophenol | 0.475 g |
| 3-Methyl-4-aminophenol | 0.535 g |
| Dye support | (*) |
| Demineralized water qs | 100 g |

(*): Common dye support:

| | |
|---|---|
| Decyl alcohol containing 3 moles of ethylene oxide | 17.5 g |
| Decyl alcohol containing 5 moles of ethylene oxide | 4.5 g |
| Lauryl alcohol containing 12 moles of ethylene oxide | 6.0 g |
| Oleocetyl alcohol containing 30 moles of ethylene oxide | 4.5 g |
| Oleic acid | 2.0 g |
| Oleyl alcohol | 1.8 g |
| Alkyl($C_{13}$/$C_{15}$)ether carboxylic acid monoethanolamide containing 2 moles of ethylene oxide | 4.0 g |
| Glycerol | 3.0 g |
| Tetramethylhexamethylene diamine/dichloro 1,3 propylene polycondensate as an aqueous solution containing 60% of A.S. (active substances) | 2.0 g |
| Merquat 280 | 2.0 g |
| Sequestering agent | qs |
| Reducing agent | qs |
| Aqueous ammonia (20% $NH_3$) | 8.0 g |
| Aculyn 44 | 0.4 g |

The composition was mixed, at the time of use, in a plastic bowl for two minutes, with an oxidizing composition given below, at a rate of 1 part of dye composition per 1.5 parts of oxidizing composition.

Oxidizing Composition:

| | |
|---|---|
| Cetylstearyl alcohol | 2.3 g |
| Cetylstearyl alcohol containing 30 moles of ethylene oxide | 0.6 g |
| Alkyl($C_{13}$/$C_{15}$ 70/30, 50% linear)ether carboxylic acid monoethanolamide containing 2 moles of ethylene oxide | 0.9 g |
| Glycerol | 0.5 g |
| Hydrogen peroxide | 7.5 g |
| Stabilizers | qs |
| Sequestering agents | qs |
| Fragrance | qs |
| Demineralized water, qs | 100 g |

The mixture obtained was applied to locks of natural hair containing 90% white hairs, and was left on for 30 minutes.

The locks were rinsed with water, washed with a standard shampoo, rinsed again and then dried.

The hair coloration was evaluated visually. The shades obtained are given in the table below.

| Tone height | Glint |
|---|---|
| Light blond | Orange-red |

What is claimed is:

1. A composition for oxidation dyeing keratin fibers, comprising, in a medium that is suitable for dyeing:
   at least one coupler chosen from 2-chloro-6-methyl-3-aminophenol and the addition salts thereof;
   at least one first oxidation base chosen from para-aminophenol and the addition salts thereof;
   at least one second oxidation base chosen from 3-methyl-4-aminophenol and the addition salts thereof; and
   at least one associative thickening polymer.

2. The composition according to claim 1, wherein the at least one associative thickening polymer comprises hydrophilic regions and hydrophobic regions that comprise at least one $C_8$-$C_{30}$ fatty chain.

3. The composition according to claim 1, wherein the at least one associative polymer is obtained by grafting a compound comprising at least one $C_8$-$C_{30}$ fatty chain onto a polymer; by free-radical polymerization starting with at least one monomer, wherein at least one of said starting monomers comprises a $C_8$-$C_{30}$ fatty chain; or by polycondensation start with at least one monomer, wherein at least one of said starting monomerscomprises a $C_8$-$C_{30}$ fatty chain.

4. The composition according to claim 1, wherein the at least one associative thickening polymer is chosen from anionic, cationic, amphoteric, and nonionic associative thickening polymers.

5. The composition according to claim 4, wherein at least one of the associative polymers is anionic.

6. The composition according to claim 5, wherein the at least one anionic associative polymer comprises at least one hydrophilic unit chosen from olefinic unsaturated carboxylic acids, and at least one hydrophobic unit chosen from ($C_{10}$-$C_{30}$)alkyl esters of unsaturated carboxylic acids.

7. The composition according to claim 5, wherein the at least one anionic associative polymer comprises acrylic acid, an acrylic or methacrylic acid ($C_{12}$-$C_{22}$)alkyl ester and a crosslinking agent.

8. The composition according to claim 7, wherein the at least one anionic associative polymer comprises from 60% to 95% by weight of acrylic acid, from 4% to 40% by weight of a $C_{10}$-$C_{30}$ alkyl acrylate and from 0% to 6% by weight of copolymerizable polyethylenic unsaturated monomer, relative to the total weight of the anionic associative polymer.

9. The composition according to claim 7, wherein the at least one anionic associative polymer comprises from 96% to 98% by weight of acrylic acid, from 1% to 4% by weight of a $C_{10}$-$C_{30}$ alkyl acrylate and from 0.1% to 0.6% by weight of crosslinking polymerizable monomer, relative to the total weight of the anionic associative polymer.

10. The composition according to claim 5, wherein the at least one anionic associative polymer is chosen from polyurethanes.

11. The composition according to claim 4, wherein at least one of the associative polymers is cationic.

12. The composition according to claim 11, wherein the at least one cationic associative polymer is chosen from quaternized cellulose derivatives.

13. The composition according to claim 12, wherein the quaternized cellulose derivatives are chosen from quaternized hydroxyethylcelluloses modified with groups comprising at least one fatty chain.

14. The composition according to claim 13, wherein the fatty chain of the hydroxyethylcelluloses is an alkyl radical comprising from 8 to 30 carbon atoms.

15. The composition according to claim 11, wherein the at least one cationic associative polymer is chosen from polyurethanes.

16. The composition according to claim 4, wherein at least one of the associative polymers is nonionic and comprises polyurethane polyethers.

17. The composition according to claim 16, wherein the polyurethane polyethers are polycondensates of polyethylene glycol containing 150 to 180 mol of ethylene oxide, of stearyl alcohol and of at least one diisocyanate.

18. The composition according to claim 17, wherein the polyurethane polyethers are polycondensates of polyethylene glycol containing 150 to 180 mol of ethylene oxide, of stearyl alcohol and of methylenebis(4-cyclohexyl isocyanate) (SMDI), at a concentration of 15% by weight in a matrix of 4% by weight of maltodextrin, and of 81% by weight of water.

19. The composition according to claim 16, wherein the polyurethane polyethers are polycondensates of polyethylene glycol containing 150 to 180 mol of ethylene oxide, of decyl alcohol and of at least one diisocyanate.

20. The composition according to claim 19, wherein the polyurethane polyethers are polycondensates of polyethylene glycol containing 150 to 180 mol of ethylene oxide, of decyl alcohol and of methylenebis(4-cyclohexyl isocyanate) (SMDI), at a concentration of 35% by weight in a mixture of 39% by weight of propylene glycol, and 26% by weight of water.

21. The composition according to claim 1, further comprising at least one additional oxidation base chosen from para-phenylenediamines, bisphenylalkylenediamines, para-aminophenols other than para-aminophenol and 3-methyl-4-aminophenol, ortho-aminophenols, heterocyclic bases, and the addition salts thereof.

22. The composition according to claims 1, comprising as the sole oxidation bases:
at least one first oxidation base chosen from para-aminophenol and the addition salts thereof; and
at least one second oxidation base chosen from 3-methyl-4-aminophenol and the addition salts thereof.

23. The composition according to claim 1, further comprising at least one additional coupler chosen from meta-phenylenediamines, meta-aminophenols, meta-diphenols other than 2-chloro-6-methyl-7-aminophenol, naphthalene-based couplers, heterocyclic couplers, and the addition salts thereof.

24. The composition according to claim 1, comprising as the sole coupler 2-chloro-6-methyl-3-aminophenol and the addition salts thereof.

25. The composition according to claim 1, wherein each oxidation base is present in the composition in an amount ranging from 0.001% to 10% by weight, relative to the total weight of the dye composition.

26. The composition according to claim 1, wherein each coupler is present in the composition in an amount ranging from 0.001% to 10% by weight, relative to the total weight of the dye composition.

27. The composition according to claim 1, further comprising at least one oxidizing agent.

28. The composition according to claim 27, wherein the at least one oxidizing agent is chosen from hydrogen peroxide, urea peroxide, alkali metal bromates, persalts, peracids and oxidase enzymes.

29. A process for oxidation dyeing keratin fibers, comprising
applying to keratin fibers a dye composition comprising, in a medium that is suitable for dyeing:
at least one coupler chosen from 2-chloro-6-methyl-3-aminophenol and the addition salts thereof;
at least one first oxidation base chosen from para-aminophenol and the addition salts thereof;
at least one second oxidation base chosen from 3-methyl-4-aminophenol and the addition salts thereof; and
at least one associative thickening polymer, and
wherein a color is developed color with at least one oxidizing agent.

30. The process according to claim 29, wherein said at least one oxidizing agent is mixed with the dye composition at the time of application, or is applied simultaneously with, or sequentially to, the dye composition.

31. The process according to claim 29, wherein which the at least one oxidizing agent is chosen from hydrogen peroxide, urea peroxide, alkali metal bromates, persalts, peracids and oxidase enzymes.

32. The process according to claim 30, wherein the at least one oxidizing agent is mixed at the time of application with the dye composition.

33. The process according to claim 29, wherein the at least one oxidizing agent is present in an oxidizing composition.

34. The process according to claim 32, wherein the oxidizing composition is applied to the keratin fibers simultaneously with, or sequentially to, the dye composition.

35. A multi-compartment kit for the oxidation dyeing of keratin fibers, comprising at least one first compartment comprising a dye composition comprising, in a medium that is suitable for dyeing:
at least one coupler chosen from 2-chloro-6-methyl-3-aminophenol and the addition salts thereof;
at least one first oxidation base chosen from para-aminophenol and the addition salts thereof;
at least one second oxidation base chosen from 3-methyl-4-aminophenol and the addition salts thereof; and
at least one associative thickening polymer, and
at least one second compartment comprising a composition comprising at least one oxidizing agent.

* * * * *